United States Patent
Harris et al.

(10) Patent No.: US 9,700,353 B2
(45) Date of Patent: Jul. 11, 2017

(54) PEDIATRIC INTERNAL MANDIBULAR DISTRACTOR

(71) Applicant: Stryker European Holdings I, LLC, Kalamazoo, MI (US)

(72) Inventors: Stephen Vaughan Harris, Redwood City, CA (US); Ediuska V. Laurens, Jersey City, NJ (US); Nathan Gorentz, Leawood, KS (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 762 days.

(21) Appl. No.: 14/090,576

(22) Filed: Nov. 26, 2013

(65) Prior Publication Data

US 2014/0148812 A1    May 29, 2014

Related U.S. Application Data

(60) Provisional application No. 61/730,194, filed on Nov. 27, 2012.

(51) Int. Cl.
*A61B 17/66* (2006.01)

(52) U.S. Cl.
CPC ............ *A61B 17/663* (2013.01); *A61B 17/66* (2013.01); *Y10T 29/49826* (2015.01); *Y10T 29/49959* (2015.01)

(58) Field of Classification Search
CPC ............................... A61B 17/66; A61B 17/663
See application file for complete search history.

(56) References Cited

U.S. PATENT DOCUMENTS

| 4,187,840 A | 2/1980 | Watanabe |
| 4,308,863 A * | 1/1982 | Fischer ............... A61B 17/62 606/56 |

(Continued)

FOREIGN PATENT DOCUMENTS

| DE | 29716635 U1 | 10/1997 |
| EP | 0998236 A1 | 5/2000 |

(Continued)

OTHER PUBLICATIONS

KLS Martin Group, "Zurich II Modular Distraction Concept", Product Brochure, 36 pages, Feb. 2007.

(Continued)

*Primary Examiner* — Nicholas Woodall
(74) *Attorney, Agent, or Firm* — Lerner, David, Littenberg, Krumholz & Mentlik, LLP (57) ABSTRACT

A pediatric mandibular distractor comprising a housing member elongating along a longitudinal axis, the housing member having at least one elongated slot elongating along at least a portion of the longitudinal axis and opening laterally through at least a side portion of the housing member; at least one fixed footplate attached to the housing member; a drive rod; and at least one moveable footplate engageable with the drive rod through the elongated slot by a connector. Wherein, when the fixed and moveable footplates are attached to the respective first and second bone surfaces, a bottom portion of the housing member is proximate to the first and second bone surfaces, and the side portion is further from the bone surfaces than the bottom portion in a direction transverse to the longitudinal axis. Methods of assembling and installing the exemplary pediatric mandibular distractor summarized above are also disclosed.

12 Claims, 7 Drawing Sheets

(56) References Cited

U.S. PATENT DOCUMENTS

| | | | |
|---|---|---|---|
| 5,364,396 A | 11/1994 | Robinson et al. | |
| 5,855,580 A * | 1/1999 | Kreidler | A61B 17/663 606/282 |
| 5,895,387 A | 4/1999 | Guerrero et al. | |
| 5,902,304 A | 5/1999 | Walker et al. | |
| 6,113,599 A | 9/2000 | Landsberger | |
| 6,203,548 B1 | 3/2001 | Helland | |
| 6,277,124 B1 | 8/2001 | Haag | |
| 6,423,069 B1 | 7/2002 | Sellers | |
| 6,471,706 B1 | 10/2002 | Schumacher et al. | |
| 6,752,808 B2 | 6/2004 | Schumacher | |
| 6,786,910 B2 | 9/2004 | Cohen et al. | |
| 6,908,469 B2 | 6/2005 | Sellers et al. | |
| 6,972,020 B1 | 12/2005 | Grayson et al. | |
| 7,252,668 B2 | 8/2007 | Wolgen | |
| 7,771,427 B2 | 8/2010 | Cohen et al. | |
| 7,875,033 B2 * | 1/2011 | Richter | A61B 17/66 606/280 |
| 8,092,463 B2 * | 1/2012 | Fuchs | A61B 17/666 606/105 |
| 8,287,573 B2 | 10/2012 | Mulone | |
| 2003/0233093 A1 | 12/2003 | Moles et al. | |
| 2005/0234448 A1 | 10/2005 | McCarthy | |
| 2006/0058785 A1 * | 3/2006 | Fuchs | A61B 17/666 606/57 |
| 2006/0058798 A1 | 3/2006 | Roman et al. | |
| 2006/0293683 A1 | 12/2006 | Stauch | |
| 2012/0259344 A1 * | 10/2012 | Johnston, Jr. | A61B 17/66 606/105 |
| 2012/0277749 A1 | 11/2012 | Mootien et al. | |
| 2014/0148812 A1 | 5/2014 | Harris et al. | |
| 2014/0163576 A1 | 6/2014 | Knoepfle et al. | |

FOREIGN PATENT DOCUMENTS

| | | |
|---|---|---|
| ES | 2167085 T3 | 5/2002 |
| WO | 9904713 A1 | 2/1999 |
| WO | 2012061987 A1 | 5/2012 |
| WO | 2012145454 A1 | 10/2012 |

OTHER PUBLICATIONS

Extended European Search Report for Application No. EP13005499 dated Feb. 6, 2014.

* cited by examiner

PEDIATRIC INTERNAL MANDIBULAR DISTRACTOR

CROSS-REFERENCE TO RELATED APPLICATIONS

The present application claims the benefit of the filing date of U.S. Provisional Patent Application No. 61/730,194 filed Nov. 27, 2012, the disclose of which is hereby incorporated herein by reference.

BACKGROUND

The present invention relates to a distractor, in particular a pediatric internal mandibular distractor for distracting bone surfaces.

The obstruction of the airway due to micrognathia is a frequent complication in infants and young children with congenital craniofacial syndromes such as Nager syndrome, Treacher Collins syndrome, and Goldenhar syndrome. These syndromes, along with specific secondary conditions such as maxillary hypoplasia in the setting of cleft lip and palate, hemifacial, microsomia, and Pierre Robin sequence, may require mandibular distraction. The small mandible causes prolapse of the tongue base against the posterior pharyngeal wall leading to respiratory distress. Particularly in young infants, airway obstruction is also commonly associated with feeding difficulties resulting in failure to thrive.

Mandibular distraction osteogenesis provides an alternative to traditional methods of airway management in infants with Pierre Robin Sequence. This approach consists of lengthening of the mandible, which allows the tongue base to move forward by its anterior muscular attachments to the mandible. Furthermore, this approach has allowed avoidance of tracheostomy as well as early decanulation in infants with Pierre Robin sequence. Tracheostomy in neonates is associated with perioperative and postoperative morbidity such as hemorrhage, pneumothorax, and tracheal stenosis.

SUMMARY OF THE INVENTION

This application discloses a pediatric mandibular distractor and related methods for assembly and installation.

An aspect of the present invention provides a pediatric mandibular distractor. The distractor in accordance with this aspect of the invention desirably comprises a housing member elongating along a longitudinal axis. The distractor may have at least one fixed footplate attached to the housing member. A drive rod may be arranged within the housing member along the longitudinal axis.

The housing member desirably has at least one elongated slot elongating along at least a portion of the longitudinal axis. The slot may open laterally through at least a side portion of the housing member. Desirably, the drive rod may be engageable with at least one moveable footplate through the elongated slot by a connector.

The fixed and moveable footplates are preferably attachable to respective first and second bone surfaces. When so attached, the bottom portion of the housing member may be proximate to the first and second bone surfaces while the side portion of housing member may be further from the bone surfaces than the bottom portion.

A number of additional aspects of the invention are also disclosed within this application. For example, each of the fixed footplate and moveable footplate may include a planar portion having a plurality of holes for receiving at least one bone screw; and each of the planar portions of the fixed and moveable footplates may be co-planar.

Another aspect of the invention is that a distal interface of the drive rod may be rotatably secured to a distal end of the housing member. Many aspects of being rotatably secured are contemplated. For example, the distal interface of the drive rod may have a channel for rotatably securing the drive rod to the housing member when a retaining pin is received in the channel. In another aspect, the distal end of the housing member may have a hole for receiving the retaining pin therein. In yet another aspect, the distal interface of the drive rod may be enclosed within the distal end of the housing member.

Aspects regarding the actuation of the pediatric mandibular distractor are also disclosed in this application. For example, a distractor in accordance with this aspect of the invention may be configured so that rotation of the drive rod advances the moveable footplate along the longitudinal axis. The drive rod may have a threaded portion and the connector of the moveable footplate may be engageable with the threaded portion of the drive rod through the elongated slot.

In another aspect, the connector may include a threaded bore and a bent portion, the threadable bore may be rotatably engageable with the drive rod, and the bent portion may extend laterally through the elongated slot. In still yet another aspect, the bent portion may comprise two substantially perpendicular bends that offset a bone attachment portion of the moveable footplate from the longitudinal axis in a direction transverse to the longitudinal axis.

Other aspects of the invention regarding the housing member are also disclosed. For example, a proximal interface of the drive rod may have an exterior dimension that is less than an interior dimension of the housing member, such that the proximal interface is receivable within the housing member to restrict lateral movement of the drive rod. In some aspects of the invention, the exterior dimension of the proximal interface may be larger than a diameter of a threaded portion of the drive rod.

Another aspect of this invention provides a method for assembling a pediatric mandible distractor. The assembly method in accordance with this aspect of the invention desirably includes providing a housing member with a fixed footplate, a moveable footplate with a connector, and a drive rod with a distal interface, the housing member elongating along a longitudinal axis. The assembly method may also include placing the connector into the housing member so that the moveable footplate extends laterally through an elongated slot in the housing member. Another aspect of the assembly method may include inserting the distal interface of the drive rod into a proximal end of the housing member. Yet another aspect of the assembly method may include engaging the connector with the drive rod. Still yet another aspect of the assembly method may include securing the distal interface of the drive rod within a distal end of the housing member. Desirably, once the distractor is assembled, actuation of the drive rod advances the moveable footplate along the longitudinal axis.

Additional aspects of the assembly method are also disclosed. For example, the elongated slot may elongate along at least a portion of the longitudinal axis and open laterally through at least a side portion of the housing member. In another aspect of the invention, the distal interface of the drive rod may have a channel; wherein the step of securing the distal interface of the drive rod within the distal end of the housing member may comprise receiving a retaining pin in the channel. In yet another aspect, the distal end of the housing member may also have a hole; wherein the step of securing the distal interface of the drive rod within the distal end of the housing member may also comprise receiving the retaining pin in the hole. In still yet another aspect, the distal interface of the drive rod may be received within an enclosed portion of the distal end of the housing member.

A further aspect of the present invention provides a method of distracting bone. The method in accordance with this aspect of the invention desirably includes attaching a fixed footplate of a distractor to a first bone surface, attaching a moveable footplate of the distractor to a second bone surface, and actuating the drive rod to advance the moveable footplate along the longitudinal axis.

In accordance with this aspect of the invention, the fixed footplate may be attached to a housing portion of the distractor. The housing portion may elongate along a longitudinal axis with at least one elongated slot elongating along at least a portion of the longitudinal axis. The elongated slot may open laterally through at least a side portion of the housing member. In another aspect, the distractor may have a drive rod, and the moveable footplate may have a connector engageable with the drive rod through the elongated slot. In another aspect, actuating the drive rod may advance the moveable footplate along the longitudinal axis.

Desirably, when the fixed and moveable footplates are attached to the respective first and second bone surfaces, a bottom portion of the housing member is proximate to the first and second bone surfaces, and the side portion is further from the bone surfaces. In some aspects of the invention, the bone may be a mandible, and the method of installation may further comprise the step of performing an osteotomy in a body, ramus, or angle of the mandible prior to attaching the fixed and moveable footplates to the respective first and second bone surfaces.

DETAILED DESCRIPTION

Figure 1A:
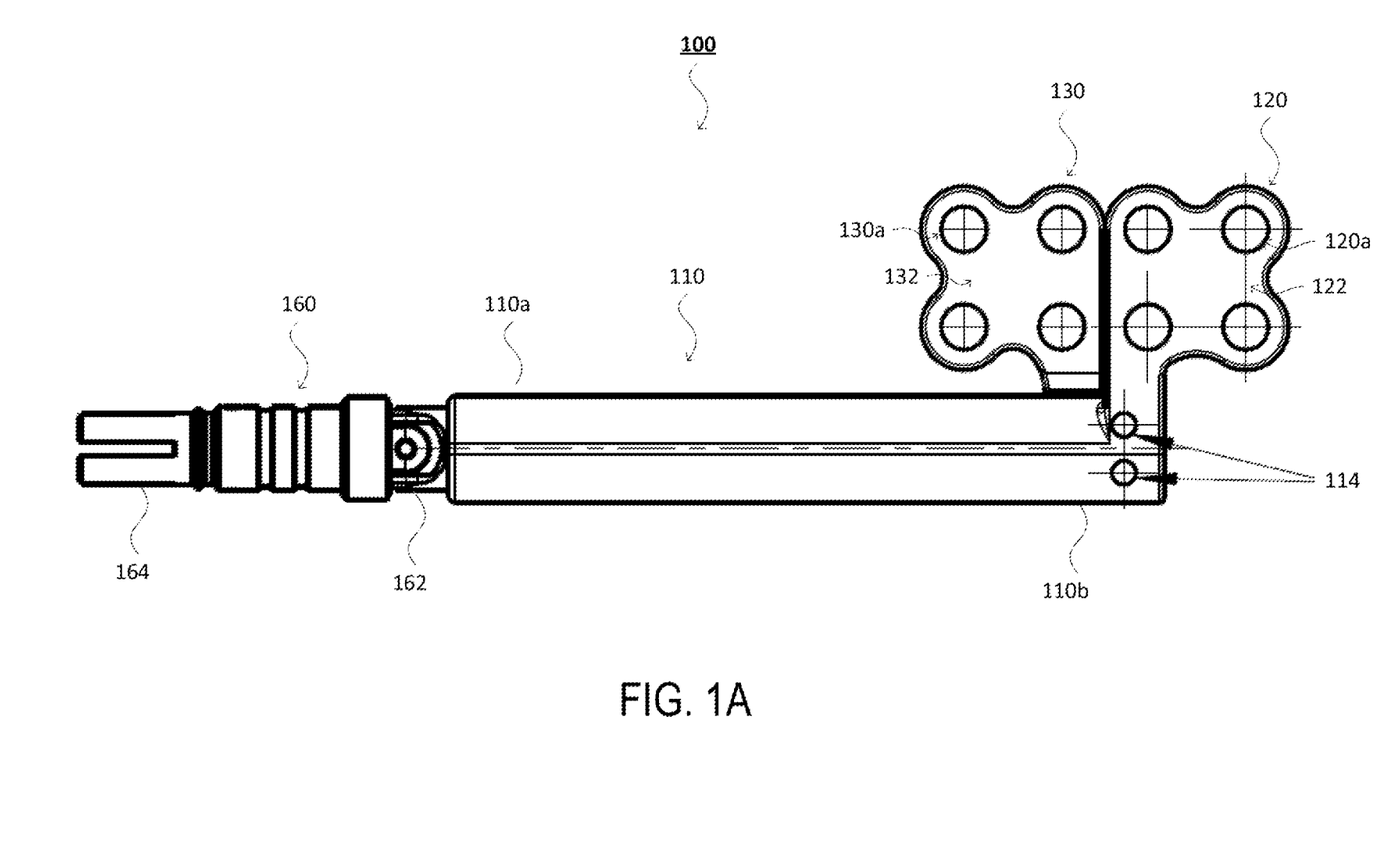
FIG. 1A is a bottom plan view and FIG. 1B is a side plan view of a distractor according to aspects of the invention.
Figure 1B:
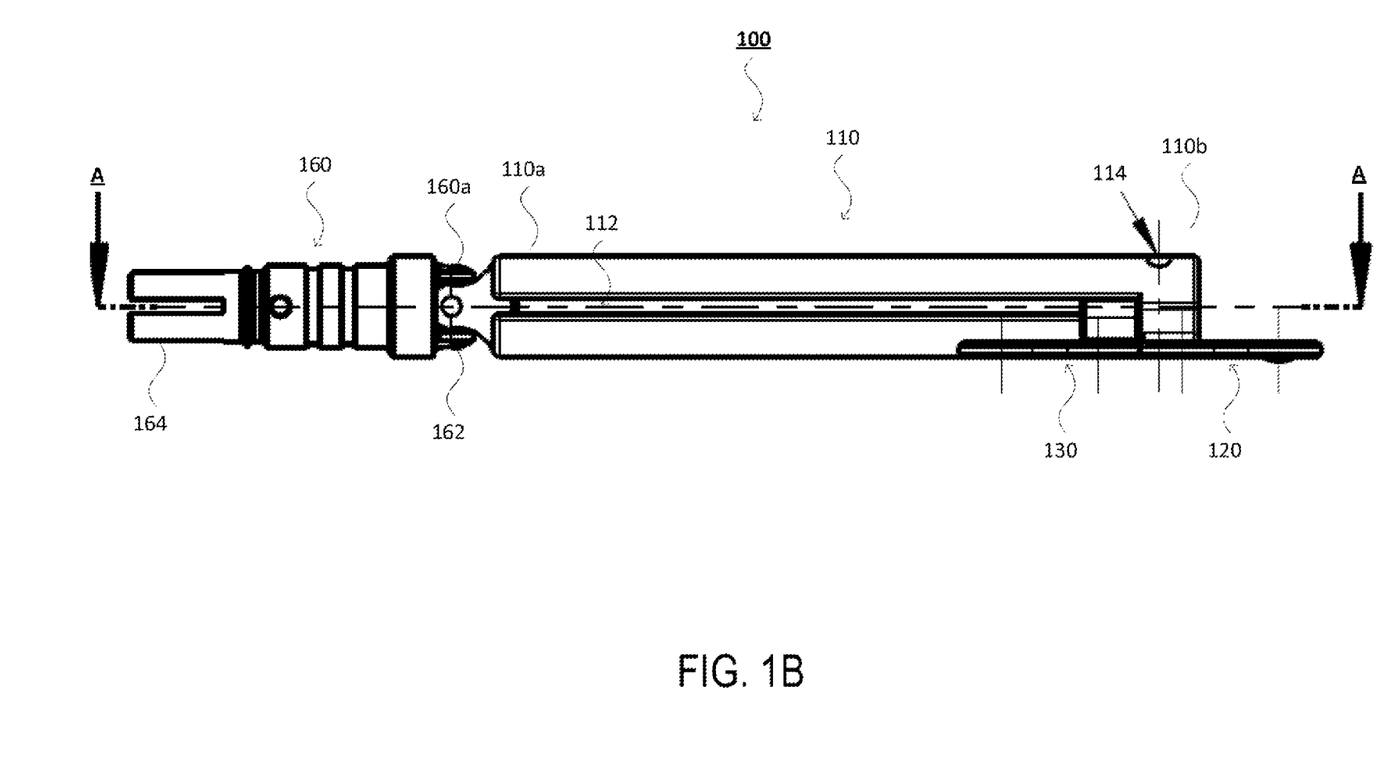
Figure 2:
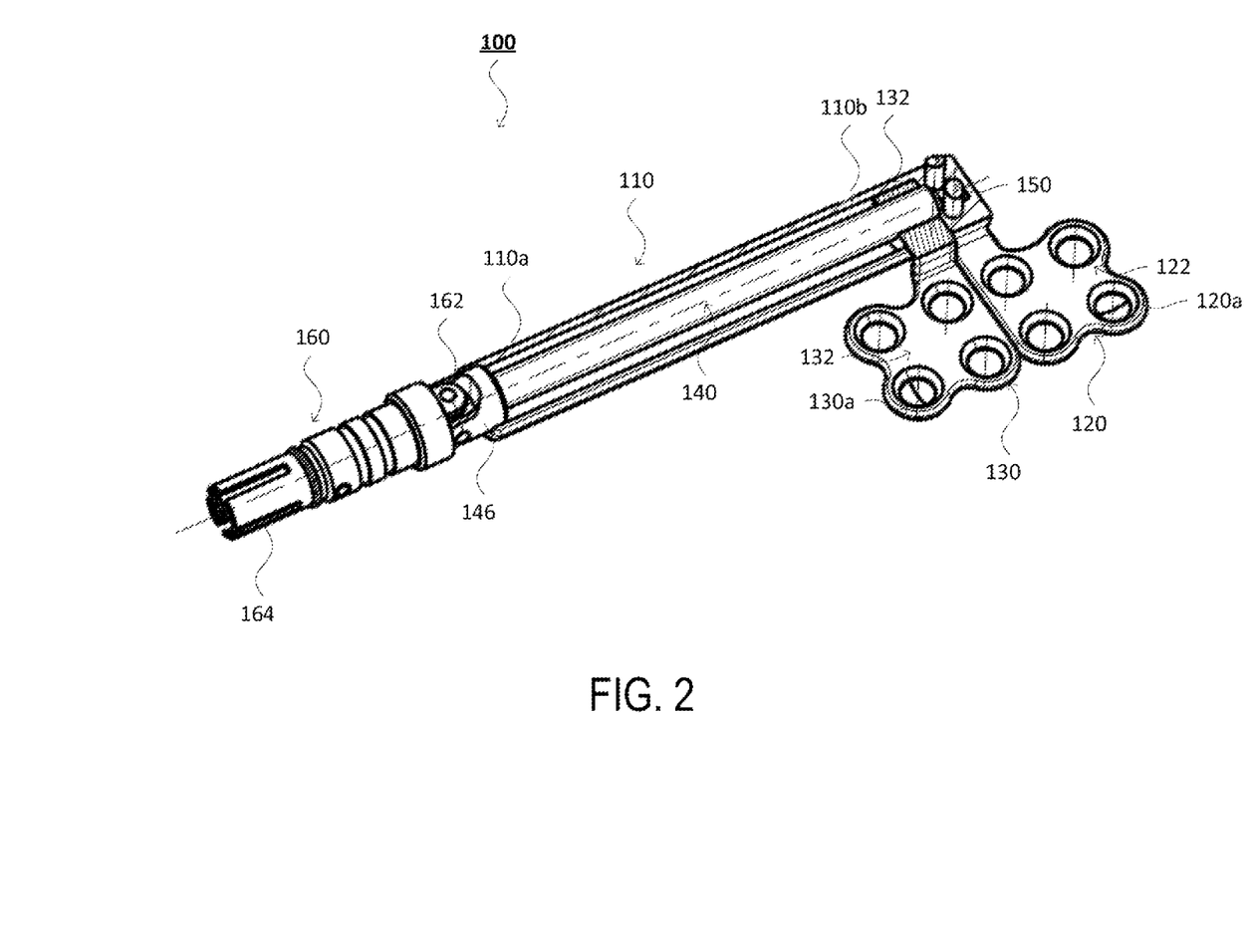
FIG. 2 is a perspective view of the distractor of FIGS. 1A and 1B with a cross-section of the housing removed along A-A.

FIGS. 1A and 1B illustrate a distractor 100 according to aspects of the invention and FIG. 2 illustrates a perspective view of the distractor of FIGS. 1A and 1B with a cross-section of the housing removed along A-A.

The distractor 100 may include a housing 110 that is generally cylindrical and extends along a longitudinal axis of the distractor 100. The housing 110 may be hollow and may include a slot 112 that extends longitudinally along the housing 110, at least partially between a proximal end 110a and a distal end 110b of the housing 110. In one example, the slot 112 may extend to the edge of the housing 110 at the proximal end 110a, but may not extend to the edge of the housing 110 at the distal end 110b. The slot 112 may have any width, and in one example may have a width sufficient to accommodate a footplate and/or footplate attachment, as will be described in greater detail below. Advantageously, the slot 112 may be positioned along a side of the housing 110 rather than along the bottom of the housing proximate the underlying bone. Desirably, the location of the slot 112 along the side of the housing reduces the risk of tissue bone ingrowth into the distractor via the slot.

The housing 110 may also include one or more holes 114. In one example, the holes 114 may be configured to receive one or more pins 150, as will be described below. The holes 114 may be formed through at least one wall of the housing 110 such that the one or more pins 150 may be inserted into the housing 110 in a direction perpendicular to the longitudinal axis. In one example, the one or more pins 150 may be inserted in a direction perpendicular to the attachment portion of one or more footplates.

Figure 4:
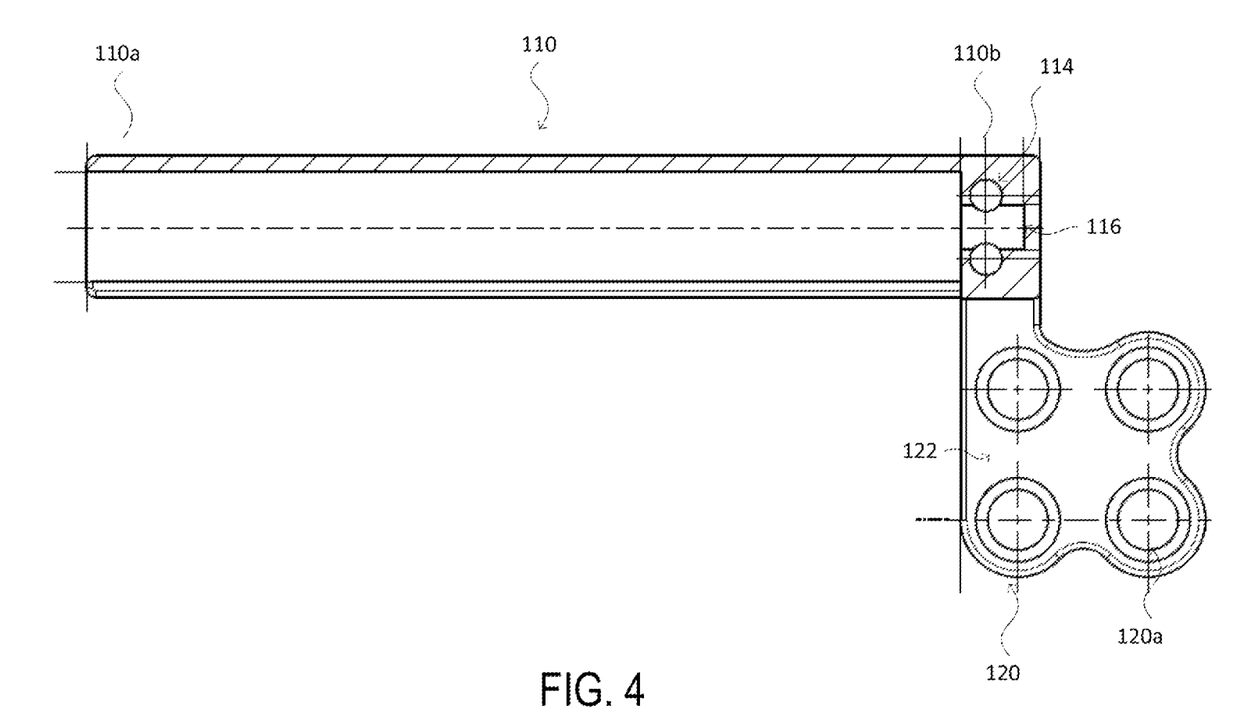
FIG. 4 is a cross-section of the housing for use with the distractor of FIGS. 1A-1B along A-A.

The housing 110 may also include a channel 116. The channel 116 may be disposed at the distal end 110b of the housing 110. The channel 116 may have an internal diameter that is less than an overall internal diameter of the housing 110, as shown in FIG. 4. The channel 116 may be positioned adjacent one or more of the holes 114 such that, when pins are inserted into the holes 114, the pins extend at least partially into the channel 116.

Figure 6:
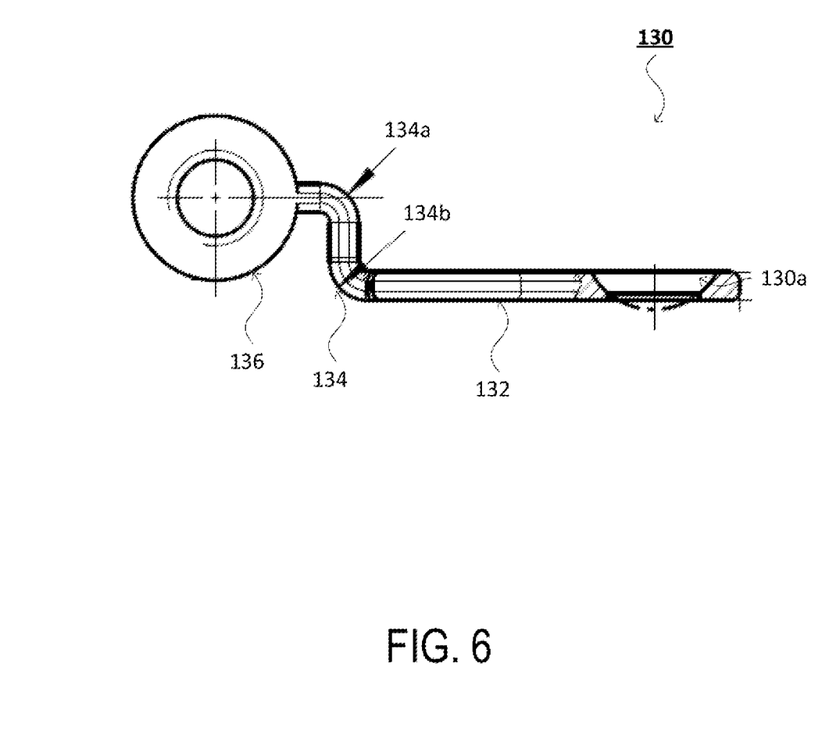
FIG. 6 is a cross-sectional view of the second footplate.

The distractor 100 may also include a first footplate 120. The first footplate 120 may be attached to the distal end 110b of the housing 110, and in one example may be fixed to, or integrally formed with, the housing 110. An attachment portion 122 of the first footplate 120 may be substantially planar and may include a plurality of holes 120a there through. The plurality of holes 120a may be aligned with a bone surface and screws (not shown) may be passed there through. This may allow the first footplate 120, and the distractor 100, to be secured to the bone surface of the patient. In one example, the plurality of holes 120a may be configured to receive resorbable screws. The holes 120a may be countersunk as shown in FIGS. 2 and 6, so that the heads of the screws may be at least partially received within the holes 120a, and, more preferably, so that the top surfaces of the screw head may be substantially flush with the top surface of the attachment portion 122.

The distractor 100 may also include a second footplate 130. The second footplate 130 may be movable with respect to the housing 110 within a slot 112, as will be explained in greater detail below. The second footplate 130 may include a footplate attachment 132 positioned within the housing 110 and a connector portion 134 extending through the slot 112 of the housing 110 from the engagement portion 136 to an attachment portion 132. The engagement portion 136 may include a threaded bore formed there through configured to threadably engage with a drive rod 140, as will be described below. An outer surface of the engagement portion 136 may be substantially cylindrical and may conform to an inner surface of the housing 110. The attachment portion 132 of the footplate 130 may be substantially planar and may include a plurality of holes 130a there through, as described above with respect to footplate 120.

As shown in FIG. 1B, the attachment portion 132 of the second footplate 130 may be positioned coplanar to the attachment portion 122 of the first footplate 120. In this arrangement, the connector portion 134 of the second footplate 130 may include two substantially perpendicular bends 134a, b in order to connect the engagement portion 136 to the attachment portion 132. In other examples, the attachment portions 122, 132 of the first and second footplates 120, 130 may be positioned orthogonal with respect to one another, or at any other desired angle suitable for the circumstances.

Figure 3:
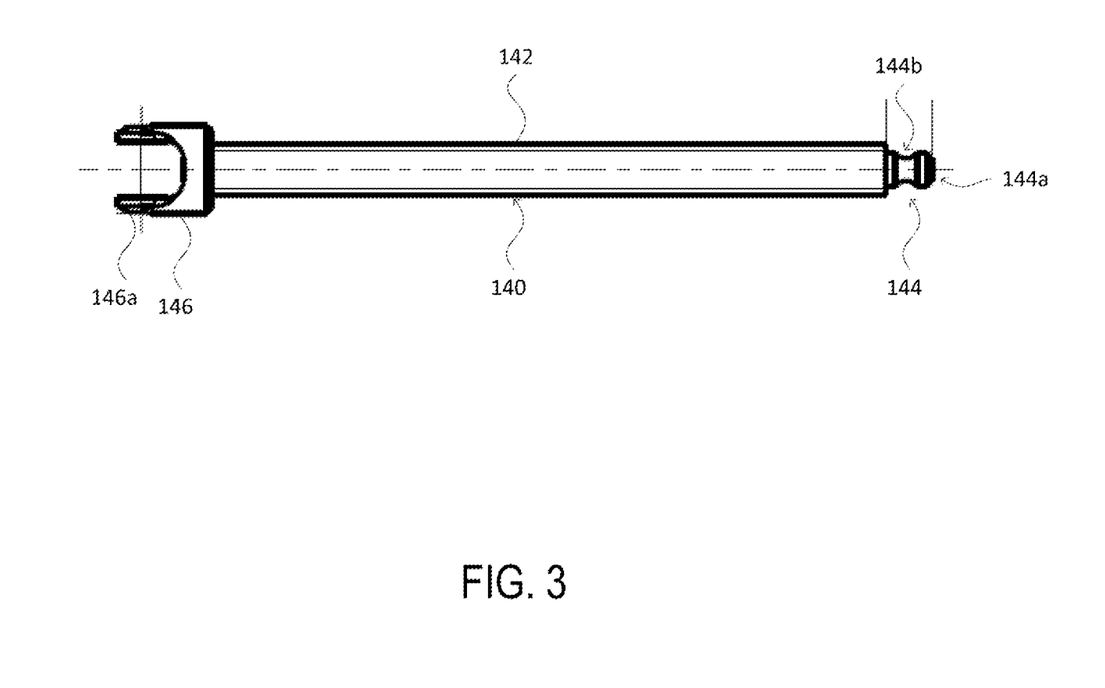
FIG. 3 is a view of the drive rod for use with the distractor of FIGS. 1A-1B.

The distractor 100 may also include a drive rod 140 arranged longitudinally within the housing 110. The drive rod may include a threaded portion 142, a projection 144, and a connection interface 146.

The threaded portion 142 may be substantially cylindrical and disposed between the projection 144 and the connection interface 146. The threaded portion may have a diameter less than an internal diameter of the housing such that the threaded portion 142 may be received within the housing 110.

One end of the drive rod 140 may include a projection 144 that extends axially with respect to the drive rod 140. The projection 144 may be cylindrical and may have a tip 144a and a channel 144b. The tip 144a may have a diameter that is larger than a diameter of the channel 144b. In this regard, the projection 144 may be secured within a corresponding channel 116 of the housing 110 by way of one or more pins 150. For example, the projection 144 may be positioned within the channel 116 such that the one or more pins 150 may partially extend into the channel 116. The one or more pins 150 may align with and engage the channel 144b of the drive rod 140, and since a clearance between the pins 150 is less than a diameter of the tip 144a of the projection 144, the drive rod 140 is restricted from moving longitudinally with respect to the housing 110. This configuration advantageously allows the distal end 110b of the housing 110 to be sealed, as the drive rod 140 does not extend through an opening at the distal end 110b of the housing, which prevents any bone or tissue from being introduced into the housing 110 through such opening.

The drive rod 140 may also include a connection interface 146 disposed at an end of the drive rod 140. The connection interface 146 may include one or more prongs 146a, b configured to interface with a connection member 160. The connection interface 146 may be at least partially cylindrical and may have a diameter greater than a diameter of the threaded portion 142. As shown in FIG. 2, the connection interface 146 may be at least partially received within the housing 110.

The diameter of the connection interface 146 may also be smaller than an interior diameter of the housing 110 such that the connection interface 146 may rotate freely about a longitudinal axis. In one example, the diameter of the connection interface 146 may be slightly less than the interior diameter of the housing 110 so as to constrain the orientation of the longitudinal axis of the drive rod 140 with respect to the housing 110. In one example, the connection interface 146 is 0.5 mm less than the interior diameter of the housing 110. As a result, the drive rod 140 may rotate freely about the longitudinal axis, but its lateral movement is restricted by the connection interface and its longitudinal movement is restricted by the pins 150, as described above.

The distractor 100 may also include a connection member 160. The connection member 160 may include one or more prongs 160a at one end for forming a joint 162 with the prongs 146a of the connection interface 146, establishing a connection between the connection member 160 and the drive rod 140. In one example, the joint 162 may be a Hooke's joint, thereby allowing rotation of the drive rod 140 by rotation of the connection member 160, or any tool attached thereto even though the connection member 160 may be angled with respect to the longitudinal axis of the drive rod 140. At the other end, the connection member 160 may include a tool interface 164 for connecting to a tool (not shown), or extension member (not shown) connectable to a tool.

The distractor 100 may be assembled by positioning the second footplate 130 within the housing 110. In this regard, the second footplate 130 may advance toward the distal end 110b of the housing 110, with the connector portion 134 advancing through the slot 112. The drive rod 140 may be inserted at the proximal end 110a of the housing 110 and may be received within the threaded bore of the engagement portion 136 of the second footplate 130 and into the channel 116. The pins 150 may then be inserted into the holes 114, thereby restricting longitudinal movement of the rod 140 with respect to the housing 110.

The distractor 100 may be installed internally within a patient, such as an infant or young child. The first and second footplates 120, 130 may be secured to respective bone surfaces within the patient by way of holes 120a and 130a and one or more bone screws. In one example, the bone surfaces may be surfaces of bone comprising the mandible, which may have an osteotomy there between. Prior to installing the distractor, the osteotomy may be performed in the body, ramus, or angle of the mandible. Once installed, the connection member 160 may be rotated in a first direction about the longitudinal axis, either alone or by way of a tool or extension member.

Figure 5:
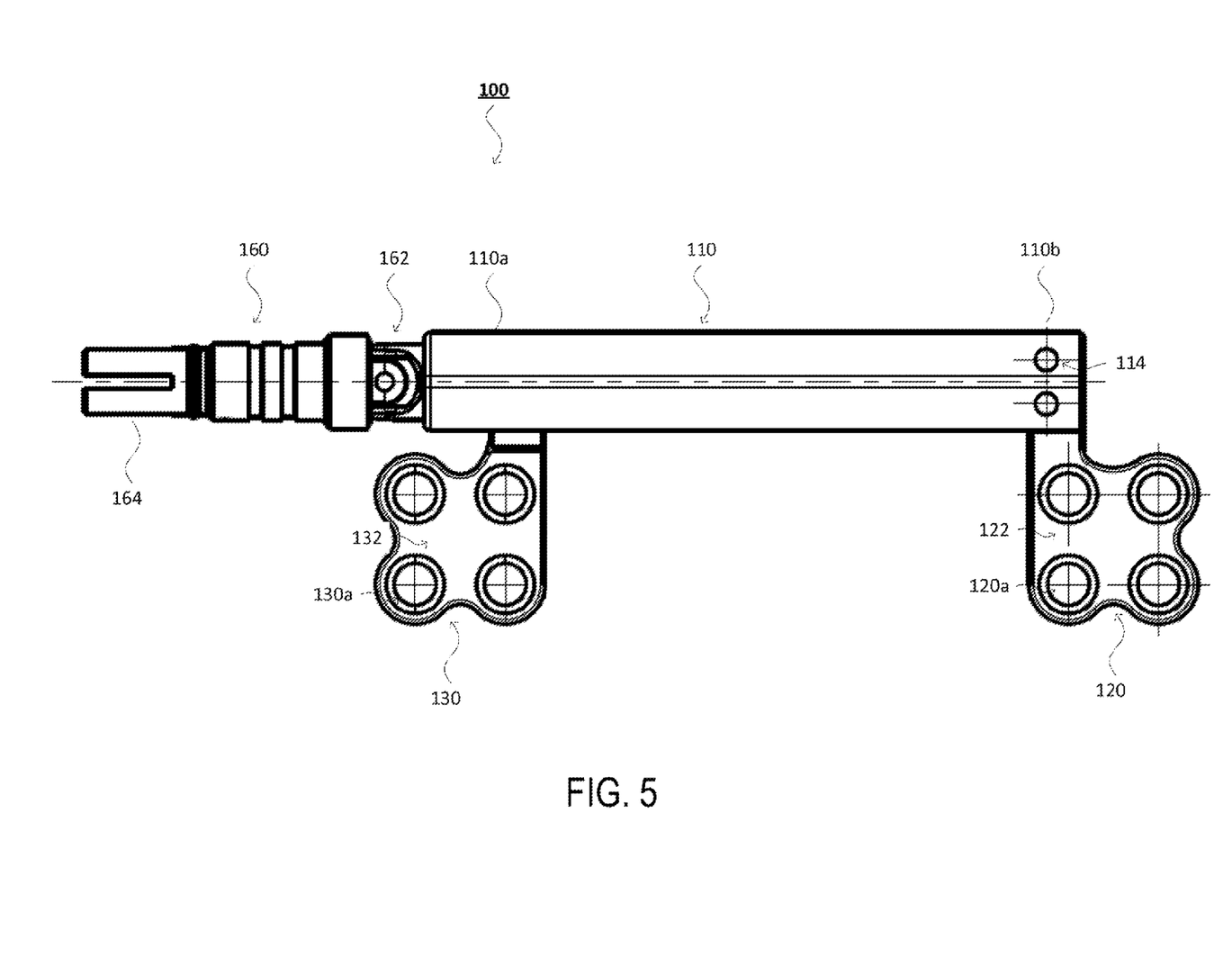
FIG. 5 is a top plan view of the distractor in an open configuration.

This rotation may cause the drive rod 140, by way of the joint 142, to similarly rotate in a first direction about the longitudinal axis. While free to rotate in this manner, the drive rod 140 is restricted from longitudinal movement, as described above, by the one or more pins 150. The drive rod 140 is also restricted from lateral movement by the interaction between the connection interface 146 and the housing 110. Since the drive rod 140 is rotating, but is longitudinally and laterally stationary, this causes the second footplate 130 to advance longitudinally along the drive rod 140 away from the first footplate 120 and toward the proximal end 110a of the housing 110, as shown in FIG. 5.

The threaded bore of the footplate attachment 132 is threadably engaged with the threaded portion 142 of the drive rod 140 and allows for longitudinal translation of the second footplate within the slot 112. As the footplates 120 and 130 are slowly moved relative to one another, bone growth may be promoted between the respective bone surfaces to which they are attached. For example, the drive rod 140 may be actuated one or more times each day and rotated a specified number of times during each actuation. If the drive rod 140 is rotated in a second direction opposite the first direction, the second footplate 130 may translate back toward the first footplate 120, thereby decreasing a distance between the two footplates 120 and 130.

The distractor 100, as well as any components thereof, may be formed of any material, and in one example may be titanium. In one example, the distractor 100 may undergo anodization, such as type II anodization. This advantageously reduces or prevents bone or tissue of a patient from attaching or adhering to the surface of the distractor 100. This allows for easy removal from the distractor 100 from the patient.

In another implementation, the distractor 100 may include a second slot disposed longitudinally along the housing 110 on an opposite side of the housing 110 from the first slot 150. In this example, a third footplate may be threadably engaged with the drive rod 140, either connected to the same footplate attachment 132 as the second footplate 130 or connected to a different footplate attachment, and may translate longitudinally along the drive rod 140 via the second slot.

In yet another implementation, the distractor 100 may include a plurality of fixed footplates, for example two or more fixed footplates. In one example, two fixed footplates may be positioned at a distal end of the housing 110, and, in another example, two fixed footplates may be positioned at the proximal end of the housing, or any combination thereof.

In the above examples, the planar attachment portions of the fixed first footplate 120 and the second footplate 130 are positioned on the same side of the longitudinal axis of the housing 110. In other examples, the first and second footplates may be positioned on opposite sides of the longitudinal axis.

Although the distraction is driven from the connection member 160 at the proximal end 110a of the housing 110 in the above examples, other implementations in accordance with aspects of the disclosure may have the distraction actuated from other locations. For example, with appropriate connections to the drive rod, the distraction may be driven from the center or at the distal end 110b of the distractor housing 110.

Although the invention herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure.

The invention claimed is:

1. An internal mandibular distractor comprising:
a housing member elongating along a longitudinal axis, the housing member having at least one elongated slot elongating along at least a portion of the longitudinal axis and opening laterally through at least a side portion of the housing member;
at least one fixed footplate attached to the housing member, the fixed footplate being attachable to a first bone surface;
a drive rod arranged within the housing member along the longitudinal axis; and
at least one moveable footplate engageable with the drive rod through the elongated slot by a connector, the movable footplate being attachable to a second bone surface,
wherein, a distal interface of the drive rod is rotatably secured to a distal end of the housing member, the distal interface of the drive rod having a channel for rotatably securing the drive rod to the housing member when a retaining pin is received in the channel, and
wherein, upon attachment of the fixed and moveable footplates to the respective first and second bone surfaces, a bottom portion of the housing member is proximate to the first and second bone surfaces, and the side portion is further from the bone surfaces than the bottom portion in a direction transverse to the longitudinal axis.

2. The internal mandibular distractor of claim 1, wherein each of the fixed footplate and moveable footplate include a planar portion having a plurality of holes for receiving at least one bone screw.

3. The internal mandibular distractor of claim 2, wherein the planar portions of the fixed and moveable footplates are co-planar.

4. The internal mandibular distractor of claim 1, wherein the distal end of the housing member has a hole for receiving the retaining pin therein.

5. The internal mandibular distractor of claim 1, wherein the distal interface of the drive rod is enclosed within the distal end of the housing member.

6. The internal mandibular distractor of claim 1, wherein rotation of the drive rod advances the moveable footplate along the longitudinal axis.

7. The internal mandibular distractor of claim 6, wherein the drive rod has a threaded portion and the connector of the moveable footplate is engageable with the threaded portion of the drive rod through the elongated slot.

8. The internal mandibular distractor of claim 7, wherein the connector includes a threaded bore and a bent portion, the threadable bore being rotatably engageable with the drive rod, and the bent portion extending laterally through the elongated slot.

9. The internal mandibular distractor of claim 8, wherein the bent portion comprises two substantially perpendicular bends that offset a bone attachment portion of the moveable footplate from the longitudinal axis in a direction transverse to the longitudinal axis.

10. The internal mandibular distractor of claim 1, wherein the housing member has an interior dimension and a proximal interface of the drive rod has an exterior dimension that is less than the interior dimension, such that the proximal interface is receivable within the housing member to restrict lateral movement of the drive rod.

11. The internal mandibular distractor of claim 10, wherein the exterior dimension of the proximal interface is larger than a diameter of a threaded portion of the drive rod.

12. The internal mandibular distractor of claim 1, wherein the channel of the distal interface of the drive rod is a circumferential channel extending around the drive rod, and wherein the retaining pin is connected to the housing member and is received in the channel to restrict the drive rod from moving longitudinally with respect to the housing member while permitting the drive rod to rotate.

* * * * *